US012421194B2

(12) United States Patent
Patra et al.

(10) Patent No.: US 12,421,194 B2
(45) Date of Patent: Sep. 23, 2025

(54) PROCESS FOR THE PREPARATION OF SUBSTITUTED PYRIDINE COMPOUNDS AND INTERMEDIATES THEREOF

(71) Applicant: PI INDUSTRIES LIMITED, Udaipur-Rajasthan (IN)

(72) Inventors: Pranab Kumar Patra, Udaipur-Rajasthan (IN); Suresh Kumar Sythana, Hyderabad (IN); Pramod Nagle, Dist-Jalgaon-Maharashtra (IN); Kantilal Balu Shende, Ahmednagar-Maharashtra (IN); Vipender Singh, Uttar Pradesh (IN); Alexander G.M. Klausener, Pulheim (DE)

(73) Assignee: PI INDUSTRIES LTD., Udaipur-Rajasthan (IN)

( * ) Notice: Subject to any disclaimer, the term of this patent is extended or adjusted under 35 U.S.C. 154(b) by 448 days.

(21) Appl. No.: 18/025,242

(22) PCT Filed: Sep. 10, 2021

(86) PCT No.: PCT/IB2021/058236
§ 371 (c)(1),
(2) Date: Mar. 8, 2023

(87) PCT Pub. No.: WO2022/053994
PCT Pub. Date: Mar. 17, 2022

(65) Prior Publication Data
US 2024/0018106 A1    Jan. 18, 2024

(30) Foreign Application Priority Data
Sep. 11, 2020 (IN) .............................. 202011039276

(51) Int. Cl.
*C07D 213/61* (2006.01)
*C07C 253/30* (2006.01)
*C07D 213/48* (2006.01)
*C07D 213/64* (2006.01)

(52) U.S. Cl.
CPC .......... *C07D 213/61* (2013.01); *C07C 253/30* (2013.01); *C07D 213/48* (2013.01); *C07D 213/64* (2013.01)

(58) Field of Classification Search
CPC .. C07D 213/61; C07D 213/48; C07D 213/64; C07C 253/30
See application file for complete search history.

(56) References Cited

U.S. PATENT DOCUMENTS 5,459,273 A      10/1995   Kraus et al.
2011/0212998 A1   9/2011   Bolli et al.

FOREIGN PATENT DOCUMENTS

CN    106866514 A      6/2017
DE      4308152 A1     9/1994
WO   2009024905 A1     2/2009

OTHER PUBLICATIONS

Robert Church et al, "New Synthetic Routes to 3-, 5-, and 6-Aryl-2-chloropyridines", The Journal of Organic Chemistry, vol. 60, No. 12, Jun. 1, 1995 (Jun. 1, 1995), p. 3750-3758, XP055357318 DOI: 10.1021/jo00117a029 external link ISSN:0022-3263.
Zhang Yinsheng et al, "A modified approach to C-14-labeled 2-(3,4-difluorophenoxy)-5-fluoronicotinic acid and other halogen-substituted analogs", Journal of Labelled Compounds and Radiopharmaceuticals, vol. 54, No. 7, Jun. 15, 2011 (Jun. 15, 2011), p. 382-386, XP055870596 DOI: 10.1002/jlcr.1887 external link ISSN:0362-4803.
Poulie Christian B. M. et al., "Design, Synthesis, and Pharmacological Characterization of Heterobivalent Ligands for the Putative 5-HT 2A /mGlu 2 Receptor Complex", Journal of Medicinal Chemistry, vol. 63, No. 17, Sep. 10, 2020 (Sep. 10, 2020), p. 9928-9949, XP055871682 DOI: 10.1021/acs.jmedchem.0c01058 external link ISSN:0022-2623.

(Continued)

*Primary Examiner* — Timothy R Rozof
(74) *Attorney, Agent, or Firm* — Lippes Mathias LLP

(57) ABSTRACT

The present invention discloses a process for the preparation of substituted pyridine compounds of formula (I), comprises a step in which vinylogous nitriles of formula (II), are obtained from substituted α,β-unsaturated nitrile compounds of formula (III), and a further step of converting the vinylogous nitrile compounds of formula (II) into substituted pyridines of formula (I); wherein $R^1$, $R^2$, $R^3$, $R^4$ and LG are as defined in the description.

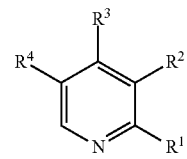

Formula (I)

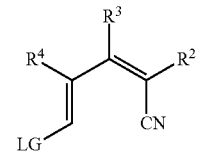

(II)

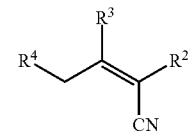

(III)

20 Claims, No Drawings

(56) References Cited

OTHER PUBLICATIONS

Hoffman J M et al, "Synthesis and Evaluation of 2-Pyridinone Derivatives as HIV-1-Specific Reverse Transciptase Inhibitors. 4. 3-Ú2-(benzoxazol-2-yl)ethyl3?4-5-ethyl-6-methylpyridin-2(1H)-one and Analogues", Journal of Medicinal Chemistry, American Chemical Society, US, vol. 36, Jan. 1, 1993 (Jan. 1, 1993), p. 953-966, XP000196096 DOI: 10.1021/JM00060A002 external link.
PCT ISR Dec. 22, 2021 (4 Pgs).
PCT WR-OPN (12 Pgs).

PROCESS FOR THE PREPARATION OF SUBSTITUTED PYRIDINE COMPOUNDS AND INTERMEDIATES THEREOF

This application is a National Stage Entry of International Application No. PCT/IB2021/058236, filed Sep. 10, 2021, which claims priority to Indian Application No. 202011039276, filed Sep. 11, 2020, the contents of which are incorporated by reference herein.

FIELD OF THE INVENTION

The present invention relates to a process for the preparation of substituted pyridines or of salts thereof. More particularly, the present invention relates to a process for the preparation of substituted pyridines of formula (I) or of salts thereof from substituted α,β-unsaturated nitrile of formula (III) or a salt thereof. The present invention further relates to a process for the preparation of vinylogous nitrile of formula (II) or of salts thereof which are useful for the preparation of compounds of formula (I) or of salts thereof.

BACKGROUND OF THE INVENTION

Substituted pyridines are essential chemical intermediates used for the preparation of pharmaceuticals and agrochemicals. In particular, 2,3-dichloropyridine is used as a starting material for the synthesis of widely applied insecticides such as Chlorantraniliprole (Rynaxypyr) and Cyantraniliprole (Cyazypyr).

There are several methods known in the literature for the synthesis of substituted pyridines.

Early reports by Baldwin et al., in *J. Org. Chem.*, 1978, 431, 2529-2535, U.S. Pat. No. 4,279,913 and *Bioorganic & Medicinal Chemistry Letters*, 19(12), 3199-3203, have described the synthesis of a variety of substituted pyridines. The condensation of alkylidene malononitrile or alkylidene cyanoacetate with either triethyl orthoformate or dimethylformamide diacetal results in the formation of equivalents of α,β,γ-unsaturated aldehydes, which undergo cyclization with acids to provide substituted pyridines.

The preparation of 2-halogeno-3-alkylsulfonylpyridines, that involves reacting N,N-dimethylacrylaldehyde with (methylsulfonyl)acetonitrile followed by reaction with HCl gas, has been reported in CN106866514.

*J. Org. Chem.*, 1995, 60(12), 3750-3758, describes the synthesis of phenyl substituted 2-halo pyridine compounds. Vinylogous enamino nitriles are synthesized using tert-butoxybis(dimethylamino)methane which is not suitable for large scale syntheses.

Several prior arts were able to achieve the synthesis of the vinylogous enamino (malono)nitriles from alkylidene (malono)nitrile/cyanoacetates/cyanosulfonyls derivatives which were easily transformed into the desired 2-halopyridine derivatives after sequential reactions. Even though much progress has been achieved, electron withdrawing (EWG) groups were crucial to obtain the requisite precursors for designated cyclizations in previously described methods.

Further, WO2012122746, CN109280026A and CN105399663A disclose a process for the preparation of a 2-halo substituted pyridine from a substituted pyridine via functional group transformation, e.g. by diazotisation reaction or by using a metal catalyst like palladium which is not economical for large scale preparations.

The use of substituted pyridines as the starting materials for the synthesis of 2,3-dihalopyridines is an expensive practice. Furthermore the use of various metal catalysts leads to the increase of steps like purification and recycling of the catalyst.

Therefore, there is a need for a process of preparation of substituted pyridines which is simple, cost-efficient and feasible on an industrial scale.

OBJECTIVE OF THE INVENTION

The main objective of the present invention is to provide a simple, environmental-friendly and cost-effective process for the preparation of substituted pyridines of formula (I) or salt thereof.

Another objective of the present invention is to provide a process for the preparation of vinylogous nitrile compounds of formula (II) or salt thereof.

SUMMARY OF THE INVENTION

Accordingly, in one aspect the present invention provides a process for the preparation of a substituted pyridines of formula (I) or salt thereof,

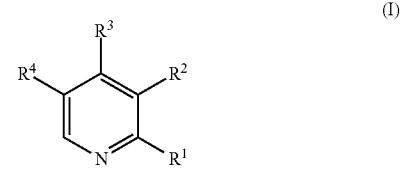

wherein
$R^1$ is selected from the group of halogen;
$R^2$ is selected from the group consisting of hydrogen, halogen, $C_1$-$C_4$ alkyl, $C_3$-$C_7$ cycloalkyl, $C_1$-$C_3$ haloalkyl, O—R', haloalkyl and O—C(O)R';
$R^3$ is selected from the group consisting of hydrogen, halogen $C_1$-$C_4$ alkyl, $C_3$-$C_7$ cycloalkyl, $C_1$-$C_3$ haloalkyl and $C_1$-$C_3$ alkoxy;
$R^4$ is selected from the group consisting of hydrogen, halogen, $C_1$-$C_4$ alkyl, $C_3$-$C_7$ cycloalkyl, $C_1$-$C_3$ haloalkyl, O—R', haloalkyl, O—C(O)R' and CHO;
R' is selected from the group consisting of $C_1$-$C_6$-alkyl and $C_1$-$C_3$ haloalkyl; or
$R^2$ and $R^3$ or $R^3$ and $R^4$ can form a 5-6 membered ring system, which is optionally substituted by halogen, $C_1$-$C_6$-alkyl, $C_1$-$C_6$-haloalkyl, $C_1$-$C_6$-alkoxy;
$R^2$, $R^3$ and $R^4$ groups are optionally substituted with halogen, CN, $C_1$-$C_6$-alkyl, $C_1$-$C_6$-haloalkyl or $C_1$-$C_6$-alkoxy;
comprising the steps of:
a) cyclizing a vinylogous nitrile of formula (II) or a salt thereof, by reacting with a suitable acid (reagent-1) and optionally in the presence of a solvent, according to the reaction scheme-1 as depicted below:

Scheme-1

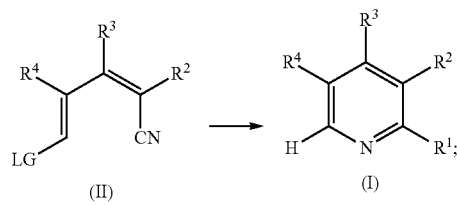

wherein LG, R', $R^1$, $R^2$, $R^3$ and $R^4$ are as defined in detailed description;

b) compound of formula (II) is obtained by reacting an α,β-unsaturated nitrile of formula (III) or a salt thereof, with reagent-2 and optionally in the presence of a catalyst and a suitable solvent, according to the reaction scheme-2 as depicted below:

Scheme-2

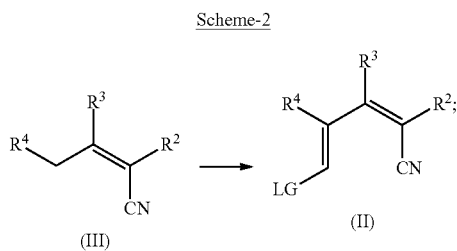

wherein,
LG, $R^2$, $R^3$, $R^4$, $R^5$, $R^6$ and $R^7$ are as defined in detailed description.

In another aspect, the present invention provides a process for the preparation of vinylogous nitriles of formula (II) or salt thereof from substituted α,β-unsaturated nitrile compounds of formula (III) or salt thereof.

In another aspect, the present invention also provides a new method for the preparation of compound of Formula (I) or a salt thereof, and wherein said method comprises of an integrated continuous flow process for reactions wherein a succession of integrated flow reactors are used to perform a series of reaction steps to yield the final product.

DETAILED DESCRIPTION OF THE INVENTION

The definitions provided herein for the terminologies used in the present disclosure are for illustrative purpose only and in no manner limit the scope of the present invention disclosed in the present disclosure.

As used herein, the terms "comprises", "comprising", "includes", "including", "has", "having", "contains", "containing", "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

Further, unless expressly stated to the contrary, "or" refers to an inclusive "or" and not to an exclusive "or". For example, a condition A "or" B is satisfied by any one of the following: A is true (or present) and B is false (or not present), A is false (or not present) and B is true (or present), and both A and B is true (or present).

Also, the indefinite articles "a" and "an" preceding an element or component of the present invention are intended to be non-restrictive regarding the number of instances (i.e. occurrences) of the element or component. Therefore "a" or "an" should be read to include one or at least one, and the singular word form of the element or component also includes the plural unless the number is obviously meant to be singular.

Carbon-based radical refers to a monovalent molecular component comprising a carbon atom that connects the radical to the remainder of the chemical structure through a single bond. Carbon-based radicals can optionally comprise saturated, unsaturated and aromatic groups, chains, rings and ring systems, and heteroatoms. Although carbon-based radicals are not subject to any particular limit in size, in the context of the present invention they typically comprise 1 to 16 carbon atoms and o to 3 heteroatoms. Of note are carbon-based radicals selected from $C_1$-$C_6$ alkyl, $C_1$-$C_6$ haloalkyl and phenyl optionally substituted with 1-3 substituents selected from $C_1$-$C_3$ alkyl, halogen, CN and nitro.

The meaning of various terms used in the description shall now be illustrated.

The term "alkyl", used either alone or in compound words such as "alkylthio" or "haloalkyl" or —N(alkyl) or alkylcarbonylalkyl or alkylsuphonylamino includes straight-chain or branched $C_1$ to $C_{10}$ alkyl, more preferably $C_1$ to $C_6$ alkyl. Representative examples of alkyl include methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl or the different isomers. If the alkyl is at the end of a composite substituent, as, for example, in alkylcycloalkyl, the part of the composite substituent at the start, for example the cycloalkyl, may be mono- or polysubstituted identically or differently and independently by alkyl. The same also applies to composite substituents in which other radicals, for example alkenyl, alkynyl, hydroxyl, halogen, carbonyl, carbonyloxy and the like, are at the end.

The term "alkoxy" used either alone or in compound words included $C_1$ to $C_{10}$ alkoxy, most preferably $C_1$ to $C_6$ alkoxy. Examples of alkoxy include methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy and the different isomers. This definition also applies to alkoxy as a part of a composite substituent, for example haloalkoxy, alkynylalkoxy, etc., unless specifically defined elsewhere.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Non-limiting examples of "haloalkyl" include chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 1,1-dichloro-2,2,2-trifluoroethyl, and 1,1,1-trifluoroprop-2-yl. This definition also applies to haloalkyl as a part of a composite substituent, for example haloalkylaminoalkyl etc., unless specifically defined elsewhere.

The term "cycloalkyl" means alkyl closed to form a ring. Representative examples include but are not limited to cyclopropyl, cyclobutyl, cyclopentyl and cyclohexyl. This definition also applies to cycloalkyl as a part of a composite substituent, for example cycloalkylalkyl etc., unless specifically defined elsewhere.

The term "cycloalkylalkyl" means cycloalkyl substituent on alkyl, for example, cyclopropyl or cyclobutyl or cyclopentyl are substituted on any carbon of $C_1$-$C_6$ alkyl. Representative examples of cycloalkylalkyl include cyclopropyl methyl, cyclopropyl ethyl.

The term "hetero" in connection with rings refers to a ring in which at least one ring atom is not carbon and which can contain 1 to 4 heteroatoms independently selected from the group consisting of nitrogen, oxygen and sulfur, provided that each ring contains no more than 4 nitrogens, no more than 2 oxygens and no more than 2 sulfurs.

The term "aromatic" indicates that the Huckel rule is satisfied and the term "non-aromatic" indicates that the Huckel rule is not satisfied.

The term "heterocycle" or "heterocyclic" or "heterocyclic ring system" includes "aromatic heterocycle" or "heteroaryl bicyclic ring system" and "nonaromatic heterocycle ring system" or polycyclic or bicyclic (spiro, fused, bridged, non-fused) ring compounds in which ring may be aromatic or non-aromatic, wherein the heterocycle ring contains at least one heteroatom selected from N, O, $S(O)_{0-2}$, and or C ring member of the heterocycle may be replaced by $C(=O)$ and $C(=S)$.

The term "non-aromatic heterocycle" or "non-aromatic heterocyclic" means three- to fifteen-membered, preferably three- to twelve-membered, saturated or partially unsaturated heterocycle containing one to four heteroatoms from the group of oxygen, nitrogen and sulphur: mono, bi- or tricyclic heterocycles which contain, in addition to carbon ring members, one to three nitrogen atoms and/or one oxygen or sulphur atom or one or two oxygen and/or sulphur atoms; if the ring contains more than one oxygen atom, they are not directly adjacent; for example (but not limited to) oxetanyl, thietanyl, oxiranyl, aziridinyl, azetidinyl, tetrahydrofuranyl, tetrahydrothienyl, pyrrolidinyl, isoxazolidinyl, isothiazolidinyl, pyrazolidinyl, oxazolidinyl, thiazolidinyl, imidazolidinyl, oxadiazolidinyl, thiadiazolidinyl, triazolidinyl, dihydrofuryl, dihydrothienyl, pyrrolinyl, isoxazolinyl, isothiazolinyl, dihydropyrazolyl, dihydrooxazolyl, dihydrothiazolyl, piperidinyl, pyrazynyl, morpholinyl, thiomorphlinyl, 1,3-dioxany, tetrahydropyranyl, tetrahydrothienyl; wherein these rings are attached to the skeleton via one of the carbon or nitrogen of said rings. This definition also applies to heterocyclyl as a part of a composite substituent, for example heterocyclylalkyl etc., unless specifically defined elsewhere.

The term "heteroaryl" or "aromatic heterocyclic" means 5 or 6-membered, fully unsaturated monocyclic ring system containing one to four heteroatoms from the group of oxygen, nitrogen and sulphur; if the ring contains more than one oxygen atom, they are not directly adjacent; 5-membered heteroaryl containing one to four nitrogen atoms or one to three nitrogen atoms and one sulphur or oxygen atom: 5-membered heteroaryl groups which, in addition to carbon atoms, may contain one to four nitrogen atoms or one to three nitrogen atoms and one sulphur or oxygen atom as ring members, for example (but not limited thereto) furyl, thienyl, pyrrolyl, isoxazolyl, isothiazolyl, pyrazolyl, oxazolyl, thiazolyl, imidazolyl, oxadiazolyl, thiadiazolyltriazolyl, tetrazolyl; wherein these rings are attached to the skeleton via one of the carbon or nitrogen of said rings.

6-membered heteroaryl which contains one to four nitrogen atoms: 6-membered heteroaryl groups which, in addition to carbon atoms, may contain, respectively, one to three and one to four nitrogen atoms as ring members, for example (but not limited thereto) pyridinyl, pyridazinyl, pyrimidinyl, pyrazinyl.

CN represents cyano group.

To achieve one or more of the above defined objectives, the present invention in a first embodiment, provides a process for the preparation of a substituted pyridine compound of formula (I) or salt thereof,

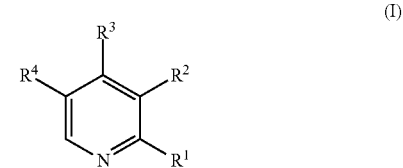

wherein,
$R^1$ is selected from the group of halogen;
$R^2$ is selected from the group consisting of hydrogen, halogen, $C_1$-$C_4$ alkyl, $C_3$-$C_7$ cycloalkyl, $C_1$-$C_3$ haloalkyl, O—R', haloalkyl and O—C(O)R';
$R^3$ is selected from the group consisting of hydrogen, halogen $C_1$-$C_4$ alkyl, $C_3$-$C_7$ cycloalkyl, $C_1$-$C_3$ haloalkyl and $C_1$-$C_3$ alkoxy;
$R^4$ is selected from the group consisting of hydrogen, halogen, $C_1$-$C_4$ alkyl, $C_3$-$C_7$ cycloalkyl, $C_1$-$C_3$ haloalkyl, O—R', haloalkyl, O—C(O)R' and CHO;
R' is selected from the group consisting of $C_1$-$C_6$-alkyl and $C_1$-$C_3$ haloalkyl; or
$R^2$ and $R^3$ or $R^3$ and $R^4$ can form a 5-6 membered ring system, which is optionally substituted by halogen, $C_1$-$C_6$-alkyl, $C_1$-$C_6$-alkoxy;
$R^2$, $R^3$ and $R^4$ groups are optionally substituted with halogen, CN, $C_1$-$C_6$-haloalkyl or $C_1$-$C_6$-alkoxy;
comprising the steps of:
a) cyclizing a vinylogous nitrile of formula (II) or salt thereof, by reacting with a suitable acid (reagent-1) and optionally in the presence of a solvent, according to the reaction scheme-1 as depicted below:

Scheme-1

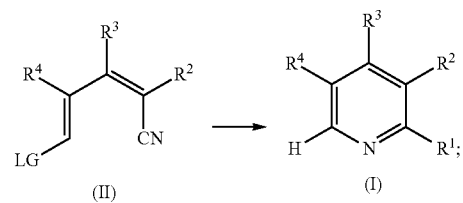

wherein LG represents OR' or N(R')$_2$; R', R$^1$, R$^2$, R$^3$ and R$^4$ are as defined above; and R$^3$ are as defined above;
b) compound of formula (II) is obtained by reacting an α,β-unsaturated nitrile of formula (III) or salt thereof, with reagent-2 and optionally in the presence of a catalyst and a suitable solvent, according to the reaction scheme-2 as depicted below:

Scheme-2

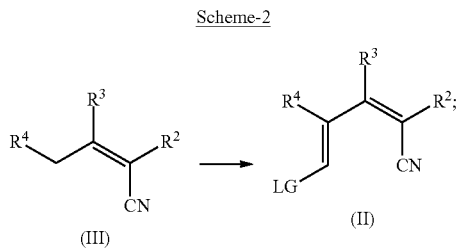

wherein,
LG, R$^2$, R$^3$ and R$^4$ are as defined above.
In one embodiment, the reagent-2 is selected from:
i. a compound of formula (R$^5$)$_2$NCH(OR$^5$)$_2$ or a salt thereof, or
ii. a compound of formula (R$^5$)$_2$NCHO or a salt thereof and co-reagent (C-1), or
iii. a suitable amine of formula NH(R$^5$)$_2$ or salt thereof, a suitable ortho esters of formula CR$^7$(OR$^5$)$_3$ or a salt thereof and co-reagent (C-2), or
iv. a suitable ortho esters of formula CR$^7$(R$^6$)$_3$ or a salt thereof and co-reagent (C-3), or
v. a suitable formic acid/ester of formula HCOOR$^7$ or a salt thereof and co-reagent (C-4), or
vi. a suitable amine of formula N(R$^5$)$_3$ or a salt thereof and co-reagent (C-5), or
vii. a carbon monoxide and co-reagent (C-4),
wherein R$^5$ represents C$_1$-C$_3$-alkyl; R$^6$ represents OR$^5$, N(R$^5$)$_2$; R$^7$ represent hydrogen or C$_1$-C$_3$-alkyl;
In a preferred embodiment, the reagent-2 is selected from:
i. a compound of formula (R$^5$)$_2$NCH(OR$^5$)$_2$ or a salt thereof, or
ii. a compound of formula (R$^5$)$_2$NCHO or a salt thereof and co-reagent (C-1), or
iii. a suitable amine of formula NH(R$^5$)$_2$ or salt thereof, a suitable ortho esters of formula CR$^7$(OR$^5$)$_3$ or a salt thereof and co-reagent (C-2),
In a more preferred embodiment, the reagent-2 is a compound of formula (R$^5$)$_2$NCH(OR$^5$)$_2$ or a salt thereof.
According to an embodiment, the co-reagent is defined as:
(C-1) represents phosphorous oxyhalides (PO(X$^1$)$_3$); wherein is halogen;
(C-2) and (C-3) represent acids such as p-toluenesulfonic acid (p-TSA), Lewis acids, (Ac)$_2$O, boron trifluoride (BF$_3$), tetrafluoroboric acid(HBF$_4$), zinc chloride (ZnCl$_2$), aluminium chloride (AlCl$_3$);
(C-4) represents a base such as sodium hydride (NaH), metal alkoxides, piperidine, pyridine, triethyl amine, N,N-diisopropylethylamine; and
(C-5) represents N,N-dimethylformamide dimethyl sulfate adduct (DMF-DMS);
In another embodiment, the multistep process as described above for preparing the compound of Formula (I) or a salt thereof, can also be performed in a continuous or semi-continuous flow process, involving either isolation or without isolation of intermediates produced during the flow process.

In a preferred embodiment, the present invention provides a process for the preparation of a compound of formula (I) or a salt thereof, wherein R$^1$ and R$^2$ represent halogen, and is represented by the formula (I-a) or a salt thereof:

Formula (I-a)

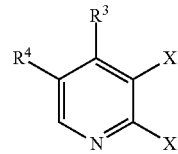

wherein
X represents halogen;
R$^3$ is selected from the group consisting of hydrogen, halogen C$_1$-C$_4$ alkyl, C$_3$-C$_7$ cycloalkyl, C$_1$-C$_3$ haloalkyl and C$_1$-C$_4$ alkoxy;
R$^4$ is selected from the group consisting of hydrogen, halogen, C$_1$-C$_4$ alkyl, C$_3$-C$_7$ cycloalkyl, C$_1$-C$_3$ haloalkyl, heterocyclyl, O—R', haloalkyl, O—C(0)R' and CHO;
R' is selected from the group consisting of C$_1$-C$_6$-alkyl and C$_1$-C$_3$ haloalkyl; or
R$^3$ and R$^4$ can form a 5-6 membered ring system, which is optionally substituted by halogen, C$_1$-C$_6$-alkyl, C$_1$-C$_6$-haloalkyl, C$_1$-C$_6$-alkoxy;
R$^3$ and R$^4$ groups are optionally substituted with halogen, CN, C$_1$-C$_6$-alkyl, C$_1$-C$_6$-haloalkyl, C$_1$-C$_6$-alkoxy;
wherein
comprising the steps of:
a) cyclizing a vinylogous nitrile of formula (II-a) or a salt thereof, by reacting it with a suitable acid (reagent-1) and optionally in the presence of a solvent, according to the reaction scheme-1a as depicted below:

Scheme-1a

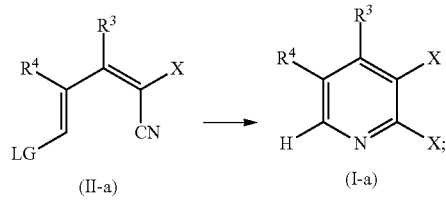

wherein X represents halogen; LG, R$^3$ and R$^4$ are as defined above;
b) compound of formula (II-a) is obtained by reacting the α,β-unsaturated nitrile of formula (III-a) or a salt thereof,
with reagent-2 and optionally in the presence of a suitable solvent, according to the reaction scheme-2a as depicted below:

Scheme-2a

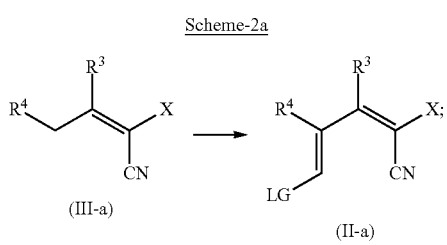

wherein X, LG, co-reagents, $R^1$, $R^2$, $R^3$, $R^3$, $R^5$, $R^6$ and $R^7$ are as defined above.

c) obtaining the α,β-unsaturated nitrile of formula (III-a) or a salt thereof,
from the substituted acrylonitrile of formula (III-b) or a salt thereof,
by halogenation, in the presence of a halogenating reagent and optionally in the presence of a reagent-3 and a suitable solvent, according to the reaction scheme-3a as depicted below:

Scheme-3a

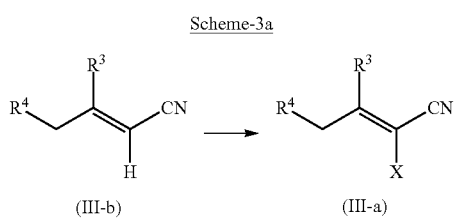

wherein X, $R^3$ and $R^4$ are as defined above.

In one embodiment, the multistep process as described above for preparing the compound of Formula (I-a) or a salt thereof, can also be performed in a continuous or semi-continuous flow process, involving either isolation or without isolation of intermediates produced during the flow process.

In one embodiment, the α,β-unsaturated nitrile of formula (III) or a salt thereof,

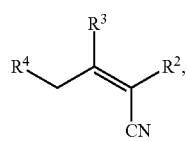

(III)

wherein $R^2$ represents halogen; $R^3$ and $R^4$ are as defined above, is prepared by, halogenating a substituted acrylonitrile of formula (III) or a salt thereof,

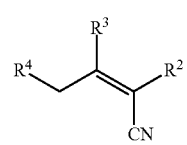

(III)

wherein $R^2$ represents hydrogen; $R^3$ and $R^4$ are as defined above; in the presence of a halogenating reagent and optionally in the presence of a reagent-3 and a solvent.

In a another embodiment, the present invention provides a process for the preparation of a compound of formula (I) or a salt thereof, wherein $R^1$ and $R^2$ represent halogen and $R^4$ is H or CHO, and is represented as a compound of formula (I-b) or a salt thereof,

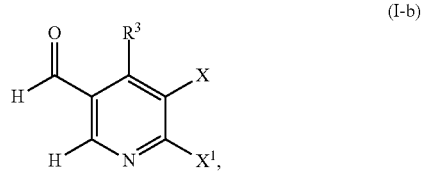

(I-b)

wherein $X^1$ represents Cl or Br; X represents F, Cl or Br. and $R^3$ is as defined above;
from the compound of formula (III-c) or salt thereof,

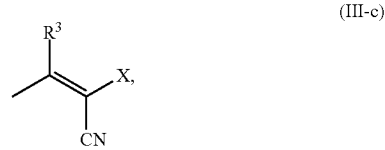

(III-c)

wherein, X and $R^3$ are as defined above; by reacting it with a mixture of N,N-dimethylformamide and phosphorous oxyhalide (DMF-PO($X^1$)$_3$), along with a compound of formula (I-a) according to the reaction scheme-4 as depicted below:

Scheme-4

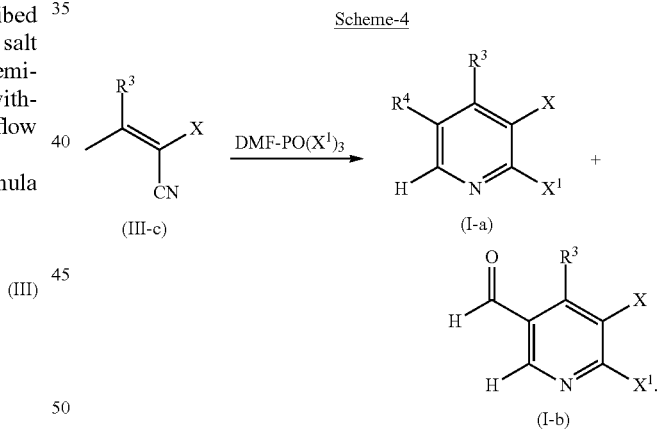

Further, in another embodiment, the present invention provides a process for the preparation of a compound of formula (II) or salt thereof, wherein LG represents —N($R^5$)$_2$, and is represented as a compound of formula (II-b) or a salt thereof,

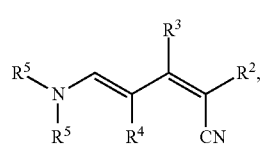

(II-b)

wherein $R^2$, $R^3$, $R^4$ and $R^5$ are as defined above;
comprising step of:
by reacting a compound of formula (III) or a salt thereof, with reagent-2 and optionally in the presence of a solvent, according to the reaction scheme-2b as depicted below:

Scheme-2b

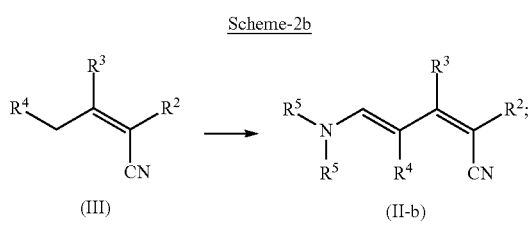

wherein $R^2$, $R^3$ and $R^4$ are as defined above.

In another embodiment, the process as described in scheme-2b for preparing the compound of formula (II-b) or a salt thereof, can also be performed in a continuous or semi-continuous flow process, involving either isolation or without isolation of intermediates produced during the flow process.

Further, yet another embodiment of the present invention provides a process for the preparation of a compound of formula (II) or a salt thereof wherein LG represents —$OR^5$, and is represented as a compound of formula (II-c) or a salt thereof,

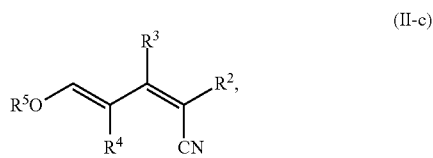

wherein $R^2$, $R^3$, $R^4$ and $R^5$ have the same meaning as defined above;
comprising the step of:
by reacting a compound of formula (III) or a salt thereof, with reagent-2 selected from:
  iv. a suitable ortho esters of formula $CR^7(R^6)_3$ or a salt thereof and co-reagent (C-3), or
  v. a suitable formic acid/ester of formula $HCOOR^7$ or a salt thereof and co-reagent ($C_4$),
and optionally in the presence of a solvent, according to the reaction scheme-2c as depicted below:

Scheme-2c

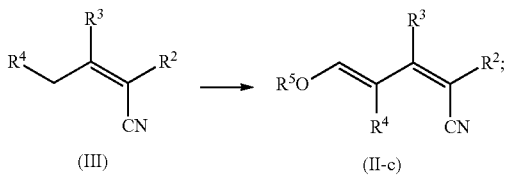

wherein $R^2$, $R^3$ and $R^4$ are as defined above.

In one embodiment, the process as described in scheme-2c for preparing the compound of Formula (II-c) or salt thereof, can also be performed in a continuous or semi-continuous flow process, involving either isolation or without isolation of intermediates produced during the flow process.

In an embodiment, the compound of formula (III-d) or salt thereof, is reacted with N,N-Dimethylformamide dimethyl acetal (DMF-DMA) to obtain a compound of formula (II-d) or a salt thereof as per the reaction scheme provided below.

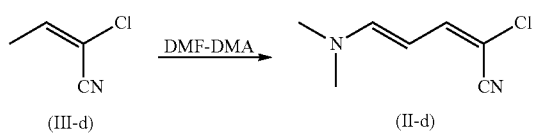

In another embodiment, the compound of formula (III-d) or a salt thereof, is reacted with trimethyl orthoformate or a salt thereof to obtain a compound of formula (II-e) or a salt thereof, as per the reaction scheme provided below.

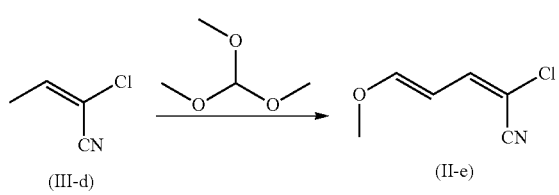

In yet another embodiment, the compound of formula (III-d) or a salt thereof, is reacted with methyl formate or a salt thereof, to obtain a compound of formula (II-f) or a salt thereof, as per the reaction scheme provided below.

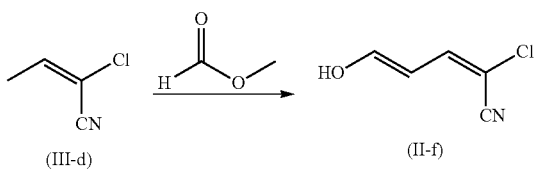

In yet another embodiment, the compound of formula (III-e) or a salt thereof, is reacted with 1,1-dimethoxy-N,N-dimethylmethanmine (DMF-DMA) to obtain a compound of formula (II-g) or a salt thereof, as per the reaction scheme provided below.

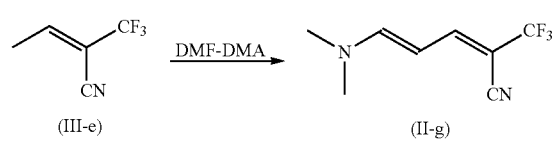

In yet another embodiment, the compound of formula (III-e) or a salt thereof, is reacted with trimethyl orthoformate or a salt thereof, to obtain a compound of formula (II-h) or a salt thereof, as per the reaction scheme provided below.

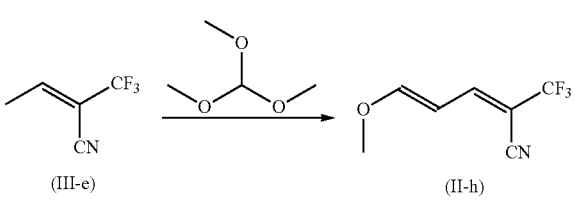

In yet another embodiment, the compound of formula (III-e) or a salt thereof, is reacted with methyl formate or salt thereof, to obtain a compound of formula (II-i) as per the reaction scheme provided below.

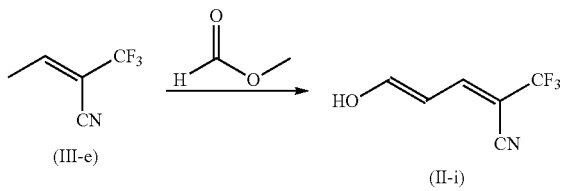

In yet another embodiment, the compound of formula (II-d) or a salt thereof, is reacted with hydrogen chloride gas to obtain a substituted pyridine of formula (I-c) or a salt thereof, as per the reaction scheme provided below.

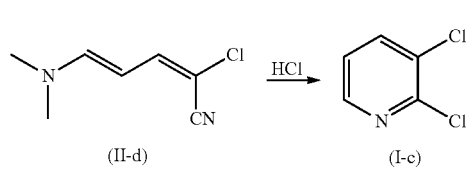

In yet another embodiment, the compound of formula (II-e) or a salt thereof, is reacted with hydrogen chloride gas to obtain a substituted pyridine of formula (I-c) or a salt thereof, as per the reaction scheme provided below.

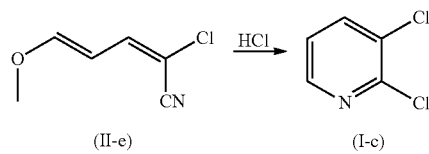

In yet another embodiment, the compound of formula (II-f) or a salt thereof, is reacted with hydrogen chloride gas to obtain a substituted pyridine of formula (I-c) or a salt thereof, as per the reaction scheme provided below.

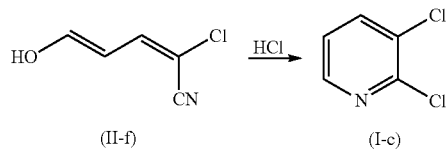 [SMILES: N#C/C(Cl)=C\C=C\O ; Cl ; Clc1cccnc1Cl]

In yet another embodiment, the compound of formula (II-g) or a salt thereof, is reacted with hydrogen chloride gas to obtain a substituted pyridine of formula (I-d) or a salt thereof, as per the reaction scheme provided below.

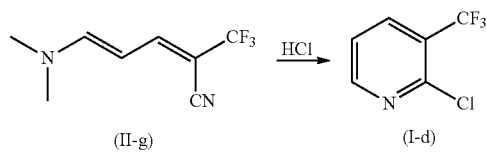

In yet another embodiment, the compound of formula (II-h) or a salt thereof, is reacted with hydrogen chloride gas to obtain a substituted pyridine of formula (I-d) or a salt thereof, as per the reaction scheme provided below.

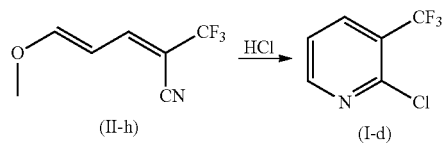

In yet another embodiment, the compound of formula (II-i) or a salt thereof, is reacted with hydrogen chloride gas to obtain a substituted pyridine of formula (I-d) or a salt thereof, as per the reaction scheme provided below.

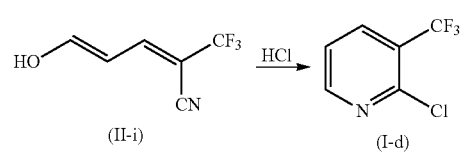 [SMILES: N#C/C(=C\C=C\O)C(F)(F)F ; Cl ; FC(F)(F)c1cccnc1Cl]

According to an embodiment, the compound of formula (I) or a salt thereof, represents compound of formula (I-a-a) or a salt thereof or compound of formula (I-b-a) or a salt thereof, wherein $R^2$ is chlorine, $R^1$ is halogen and can be prepared from the compound of formula (III-d) or a salt thereof by halogenating with a halogenating agent and N,N-dimethylformanide, as per the reaction scheme provided below.

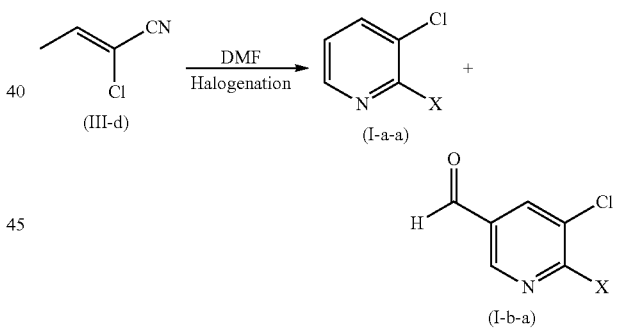

In accordance with the embodiments of the present disclosure, the heating can be carried out at a temperature between 40° C. to 100° C.

Typically, the compound of formula (III-d) or a salt thereof, is reacted with phosphoryl chloride in N,N-dimethylformamide at 80° C. to obtain a substituted pyridine of formula (I-c) and a substituted compound of formula of (I-b-b), as per the reaction scheme provided below.

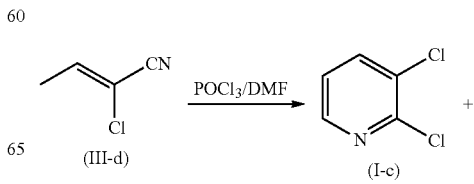

-continued

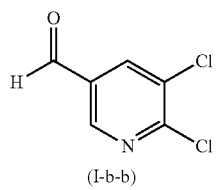
(I-b-b)

Typically, the compound of formula (III-e) or a salt thereof, is reacted with phosphoryl chloride in dimethyl formamide at 80° C. to obtain a substituted pyridine of formula (I-d) or a salt thereof and a substituted pyridine of formula (I-b-c) or a salt thereof, as per the reaction scheme provided below.

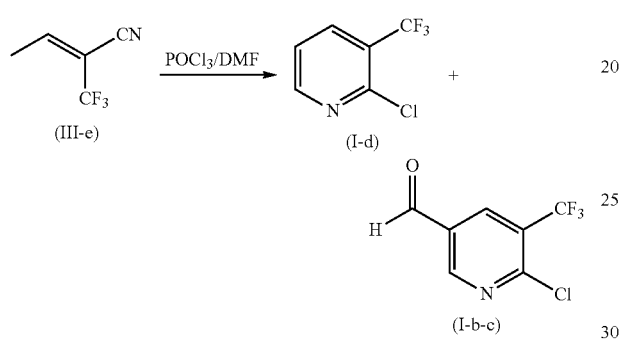

In yet another embodiment, the present invention provides a process for the preparation of a substituted 2-hydrazineyl pyridine of formula (VI) or a salt thereof,

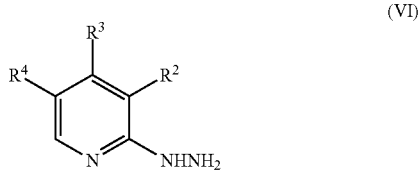
(VI)

wherein,
$R^2$ is selected from the group consisting of hydrogen, halogen, $C_1$-$C_4$ alkyl, $C_3$-$C_7$ cycloalkyl, $C_1$-$C_3$ haloalkyl, heterocyclyl, O—R', haloalkyl and O—C(O)R';
$R^3$ is selected from the group consisting of hydrogen, halogen $C_1$-$C_4$ alkyl, $C_3$-$C_7$ cycloalkyl, $C_1$-$C_3$ haloalkyl and $C_{1-3}$ alkoxy;
$R^4$ is selected from the group consisting of hydrogen, halogen, $C_1$-$C_4$ alkyl, $C_3$-$C_7$ cycloalkyl, $C_1$-$C_3$ haloalkyl, heterocyclyl, O—R', haloalkyl, O—C(O)R' and CHO;
R' is selected from the group consisting of $C_1$-$C_6$-alkyl and $C_1$-$C_3$ haloalkyl; or
$R^2$ and $R^3$ or $R^3$ and $R^4$ can form a 5-6 membered carbocyclic or heterocyclic ring system, which is optionally substituted by halogen, $C_1$-$C_6$-alkyl, $C_1$-$C_6$-haloalkyl, $C_1$-$C_6$-alkoxy;
$R^2$, $R^3$ and $R^4$ groups are optionally substituted with halogen, CN, $C_1$-$C_6$-alkyl, $C_1$-$C_6$-haloalkyl, $C_1$-$C_6$-alkoxy;
wherein, the said process comprises reaction of a substituted pyridine of formula (I) or a salt thereof prepared according to anyone of the process, as described in the aforementioned embodiments,

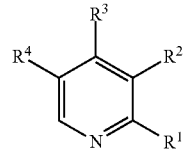

wherein, $R^1$ is halogen and $R^2$, $R^3$, $R^4$ are as defined above, with hydrazine source and optionally in presence of base and a solvent as depicted in scheme below:

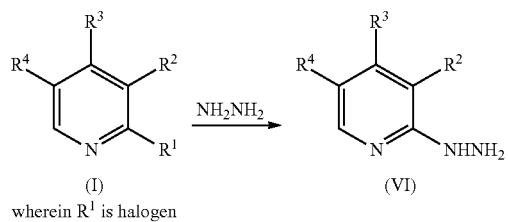
wherein $R^1$ is halogen

The hydrazine source is selcted from hydrazine hydrate, hydrazine suphate or hydrazine chloride.

In further embodiment, the present invention provides an integrated, continuous or semicontinuous flow process for the preparation of a compound of formula (I) or salt thereof,

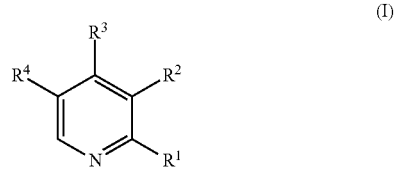
(I)

wherein,
$R^1$ is selected from the group of halogen and $C_1$-$C_4$ alkoxy;
$R^2$ is selected from the group consisting of hydrogen, halogen, $C_1$-$C_4$ alkyl, $C_3$-$C_7$ cycloalkyl, $C_1$-$C_3$ haloalkyl, heterocyclyl, O—R', haloalkyl and O—C(O)R';
$R^3$ is selected from the group consisting of hydrogen, halogen $C_1$-$C_4$ alkyl, $C_3$-$C_7$ cycloalkyl, $C_1$-$C_3$ haloalkyl and $C_1$-$C_4$ alkoxy;
$R^4$ is selected from the group consisting of hydrogen, halogen, $C_1$-$C_4$ alkyl, $C_3$-$C_7$ cycloalkyl, $C_1$-$C_3$ haloalkyl, heterocyclyl, O—R', haloalkyl, O—C(O)R' and CHO;
R' is selected from the group consisting of $C_1$-$C_6$-alkyl and $C_1$-$C_3$ haloalkyl;
wherein $R^3$ and $R^4$ can form a 5-6 membered ring system, which is optionally substituted by halogen, $C_1$-$C_6$-alkyl, $C_1$-$C_6$-haloalkyl, $C_1$-$C_6$-alkoxy;
$R^3$ and $R^4$ groups are optionally substituted with halogen, CN, $C_1$-$C_6$-alkyl, $C_1$-$C_6$-haloalkyl, $C_1$-$C_6$-alkoxy;
comprising the steps of:
A. cyclizing a vinylogous nitrile of formula (II) or a salt thereof,
by reacting with a suitable acid (reagent-1) and optionally in the presence of a solvent, according to the reaction scheme-1 as depicted below:

Scheme-1

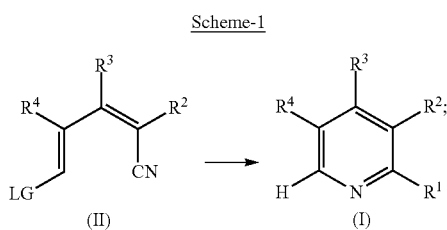

wherein LG represents OR' or N(R')$_2$; R', R$^1$, R$^2$, R$^3$ and R$^4$ are as defined above;

B. compound of formula (II) is obtained by reacting an α,β-unsaturated nitrile of formula (III) or a salt thereof, with reagent-2 selected from:
  i. with a compound of formula (R$^5$)$_2$NCHO or a salt thereof and co-reagent (C-1) or
  ii. with a suitable amine compound of formula NH(R$^5$)$_2$ or a salt thereof, suitable ortho esters compound of formula CR$^7$(OR$^5$)$_3$ or a salt thereof and co-reagent (C-2), and optionally in the presence of a suitable solvent, according to the reaction scheme-2 as depicted below:

Scheme-2

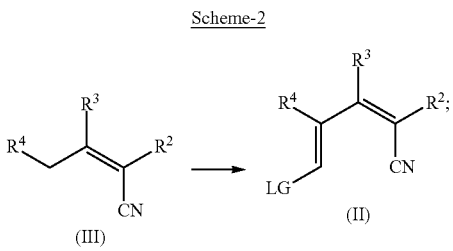

wherein, LG, co-reagents, R$^1$, R$^2$, R$^3$, R$^4$, R$^5$, R$^6$ and W are as defined above;

In another embodiment, the present invention provides an integrated, continuous or semicontinuous flow process for the preparation of a compound of formula (I) or salt thereof,

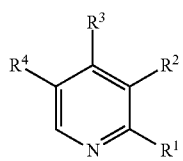

wherein,

R$^1$ and R$^2$ represents halogen; and R$^3$ and R$^4$ are same as defined above.

comprising the steps of:

A. cyclizing a vinylogous nitrile of formula (II) or a salt thereof, by reacting with a suitable acid (reagent-1) and optionally in the presence of a solvent, according to the reaction scheme-1 as depicted below:

Scheme-1

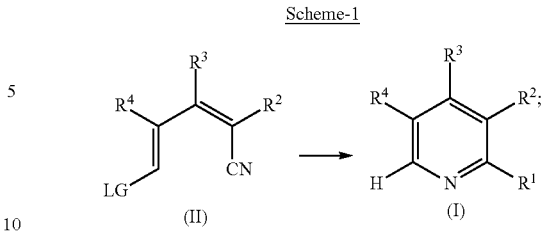

wherein LG represents OR' or N(R')$_2$; R', R$^1$, R$^2$, R$^3$ and R$^4$ are as defined above;

B. compound of formula (II) is obtained by reacting an α,β-unsaturated nitrile of formula (III) or a salt thereof, with reagent-2 selected from:
  i. with a compound of formula (R$^5$)$_2$NCHO or a salt thereof and co-reagent (C-1) or
  ii. with a suitable amine of formula NH(R$^5$)$_2$ or a salt thereof, suitable ortho esters of formula CR$^7$(OR$^5$)$_3$ or a salt thereof and co-reagent (C-2), and optionally in the presence of a suitable solvent, according to the reaction scheme-2 as depicted below:

Scheme-2

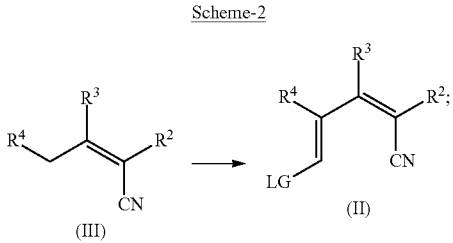

wherein, LG, co-reagents, R$^1$, R$^2$, R$^3$, R$^4$, R$^5$, R$^6$ and R$^7$ are as defined above;

C. obtaining the α,β-unsaturated nitrile of formula (III) or a salt thereof,
  from a substituted acrylonitrile compounds of formula (III-b) or a salt thereof,
  by halogenation, in the presence of a halogenating reagent and optionally in the presence of a reagent-3 and a suitable solvent, according to the reaction scheme-3a as depicted below:

Scheme-3a

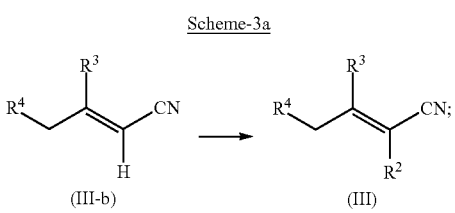

wherein R$^2$ is halogen; R$^3$ and R$^4$ are as defined above.

According to an embodiment, reagent-1 includes but is not limited to an acid such as inorganic acid selected from hydrogen fluoride, hydrogen chloride or hydrogen bromide; metal complex such as a Lewis acid selected from titanium tetrachloride, boron trifluoride etherate, copper chloride, aluminium trichloride and zinc chloride.

In one embodiment, the reaction of converting α,β-unsaturated nitrile of formula (III) or a salt thereof, to vinylogous nitriles of formula (II) is carried out optionally in the presence of a suitable solvent with a suitable compound of formula $(R^5)_2NCH(OR^5)_2$ or a salt thereof or a suitable amine of formula $NH(R^5)_2$ or a salt thereof and suitable ortho esters of formula $CR^7(OR^5)_3$ or salt thereof; optionally in the presence of co-reagent at a temperature within the range of 20° C. to 130° C.

The suitable solvents as used in any of the process steps of the present invention are selected from aliphatic, alicyclic or aromatic hydrocarbons such as, petroleum ether, hexane, heptane, cyclohexane, methylcyclohexane, toluene, xylene or decalin; aliphatic, alicyclic or aromatic halogenated hydrocarbons such as chlorobenzene, dichlorobenzene, dichloromethane, chloroform, tetrachloromethane, dichloroethane or trichloroethane; ethers such as diethylether, diisopropyl ether, methyl tert-butyl ether, methyl tert-amyl ether, dioxane, tetrahydrofuran, 1,2-dimethoxy ethane, 1,2-diethoxyethane or anisole; nitriles such as acetonitrile, propionitrile, n- or iso-butyronitrile or benzonitrile; amides such as N,N-dimethylformamide, N,N-dimethylacetamide, N-methylformanilide, N-methylpyrrolidone or hexamethylphosphoric triamide; sulfoxides such as dimethyl sulfoxide or sulfones such as sulfolane; alcohols such as methanol, ethanol, isopropanol, polyethylene glycols; water or mixtures thereof.

The suitable solvents for halogenation reaction (Step-c)) are aliphatic, alicyclic or aromatic halogenated hydrocarbons such chlorobenzene, dichlorobenzene, dichloromethane, chloroform, tetrachloromethane, dichloroethane, trichloroethane; preferably dichloromethane, chloroform, dichloroethane, trichloroethane.

The suitable solvents for preparing vinylogus nitrile reaction (step-b) are aliphatic, alicyclic or aromatic hydrocarbons such as, heptane, cyclohexane, methylcyclohexane, toluene, xylene or decalin; amides such as N,N-dimethylformamide, N,N-dimethylacetamide, N-methyl formanilide, N-methylpyrrolidone; alcohols such as methanol, ethanol, isopropanol; ethers such as 1,2-dimethoxy ethane, 1,2-diethoxyethane dioxane; toluene, sulfoxides such as dimethyl sulfoxide or sulfones such as sulfolane;

The suitable solvents for cyclisation reaction (Step-a) aliphatic, alicyclic or aromatic halogenated hydrocarbons such as chlorobenzene, dichlorobenzene, dichloromethane, chloroform, tetrachloromethane, dichloroethane or trichloroethane; ethers such as diethylether, diisopropyl ether, methyl tert-butyl ether, methyl tert-amyl ether, dioxane, tetrahydrofuran, 1,2-dimethoxy ethane, 1,2-diethoxyethane or anisole; alcohols such as methanol, ethanol, isopropanol, polyethylene glycols; acetic acid or mixtures thereof.

In one embodiment and in a non limiting way, the halogenating agent used in step-c is either chlorine gas, or hydrogen halogenides such as hydrogen fluoride, hydrogen chloride or hydrogen bromide, along with oxidizing reagents such as hydrogen peroxide In one embodiment, the reagent-3 used in the halogenation/chlorination reaction (step-c) includes but is not limited to pyridine, lutidine, hydroquinone, piperidine and triethylamine, diisopropyl ethyl amine, pyridine, alkylated and dialkylated pyridines, 1,8-Diazabicyclo[5.4.0]undec-7-ene (DBU), 1,4-diazabicyclo[2.2.2]octane (DABCO), or inorganic bases are preferably selected from the group comprising of alkali or alkaline earth metal hydroxide, carbonate, bicarbonate and the like, wherein the alkali and alkaline earth metals are selected from the group comprising of lithium, sodium, potassium, rubidium, caesium, calcium, magnesium, barium and the like or of mixtures thereof. Preferably, triethylamine, diisopropyl ethyl amine, pyridine, hydroquinone, sodium carbonate, potassium carbonate or of mixtures; more preferably triethylamine, hydroquinone, potassium carbonate or of mixtures;

In one embodiment, the catalyst used in the condensation reaction(step-b) includes but is not limited to acetic anhydride and p-toluene sulfonic acid.

In one embodiment, preferred reagent-1 used in the cyclisation reaction (step-a) includes but is not limited to an acid such hydrogen fluoride, hydrogen chloride or hydrogen bromide.

An embodiment of the present invention provides an integrated continuous flow process for step A, for the preparation of compound of formula (I) or a salt thereof, comprising, reacting a vinylogous nitrile of formula (II) or a salt thereof, with a suitable acid (reagent-1) and optionally in the presence of solvent (according to the reaction scheme-1), in a suitable reactor, wherein LG, R', $R^1$, $R^2$, $R^3$ and $R^4$ are as defined above. The residence time of the mixture in the reactor typically ranges anywhere between 30 seconds and 30 minutes, preferably about 30 seconds to 10 minutes depending on the temperature. The temperature in the reactor is typically anywhere between 0° C. and 150° C., preferably between 10° C. and 100° C.

Optionally, all flow the reactors may be connected with batch equipment to get the right puritybefore introducing the flow in the following continuous reaction step.

Another embodiment of the present invention provides an integrated continuous flow process for step B, for the preparation of compound of formula (II) or a salt thereof, comprising, reactinig an α,β-unsaturated nitrile of formula (III-a) with any one of the reagents selected from group (i to vii) as described above (according to the reaction scheme-2) in a suitable reactor, wherein, LG, co-reagents, $R^1$, $R^2$, $R^3$, $R^4$, $R^5$, $R^6$ and $R^7$ are as defined above. The residence time of the mixture in the reactor is typically anywhere between 30 seconds and 30 minutes, preferably about 30 seconds to 10 minutes, and more preferably 30 seconds to 5 minutes depending on the temperature. The temperature in the reactor is typically anywhere between 0° C. and 150° C., preferably between 0° C. and 100° C.

A further embodiment of the present invention provides an integrated continuous flow process for step C, for the preparation of compound of formula (III-a) or a salt thereof, comprising, halogenating a substituted acrylonitrile of formula (III-b) or a salt thereof, with a halogenating reagent and optionally in the presence of a catalyst and in a suitable solvent (according to the reaction scheme-3a) in a suitable reactor, wherein X, $R^3$ and $R^3$ are as defined above. The residence time of the mixture in the reactor is typically anywhere between seconds and 30 minutes, preferably about 30 seconds to 10 minutes, and more preferably 30 seconds to 5 minutes depending on the temperature. The temperature in the reactor is typically anywhere between 0° C. and 150° C., preferably between 10° C. and 120° C.

All the reactions steps A to C as described above are performed in flow reactors connected to each other in such a way as to provide an integrated system. There are many configurations of such connected reactor system, that a person skilled in the art is aware of.

Translating reactions into continuous-flow system is aiding more efficient, safer, and automated reactions. The ability of continuous-flow system to rapidly heat and cool reactions, micromix solutions, and improve reaction homogeneity affords opportunities to explore novel transformations while being environmentally conscious and creative.

The injected fluid flows into reactor coils where the specific transformation is subjected to a range of conditions.

For example, the fluid entering the reactor coil can be rapidly heated or cooled to mediate an effective transformation.

The efficiency of the continuous or semi-continuous flow process depends upon several factors, some of which include temperature of the reactor, residence time, flow rate of the reactant mixture, pressure within the reactor. A persone skilled in the art can optimise the efficiency of the flow process by varying these factors.

In the context of the present invention, the term "without isolation" means that the product referred is not isolated, for example it is not isolated from the reaction mass and dried/concentrated to obtain a solid/sticky mass/liquid. Thus, "without isolation" may mean that the product remains insolution and is then used directly in the next synthetic step.

The residence time of the fluid within the system is determined by the internal diameter and length of the reactor coil.

Mixers and unions connect reactor coils together and allow the addition of new reagents to the continuous-flow stream. The solution can be flowed through packed bed reactors to ensure efficient mixing, or to provide exposure to immobilized reagents for synthetic transformations.

A continuous-flow system allows the possibility of in-line purification and reagent introduction at set points in the continuous-flow sequence.

Depending on the nature of the substituents, the intermediates as mentioned in the described schemes or compounds of formula such as (II) or (III) or a salt thereof, can also exist in one or more geometric isomer forms depending on the relative position (cis/trans) of the substituents. The invention thus relates equally to all cis/trans isomers and to all possible cis/trans mixtures, in all proportions. The cis/trans isomers can be separated according to general methods, which are known by a person having ordinary skilled in the art.

The compounds of the present disclosure may be present either in pure form or as mixtures of different possible isomeric forms such as geometric isomers. Any desired mixtures of these isomers fall within the scope of the claims of the present disclosure.

The processes as disclosed in the present invention can be run in the absence of a solvent or in the presence of one or more suitable solvents. The optional solvent should be resistant against oxidation (i.e. a solvent will be preferred whose rate of oxidation is substantially slower than that of the compounds of formula I to III) and suitable for suspending, or preferably dissolving the reactants.

Any person skilled in the art knows the best work-up of the reaction mixtures after the end of the respective reactions. In one embodiment, the work-up is usually carried out by isolation of the product by filtration, and optionally washing with solvent, further optionally drying of the product if required.

The process steps according to the invention are generally carried out under atmospheric pressure. Alternatively, however, it is also possible to carry out the reaction under pressure or reduced pressure.

Without further elaboration, it is believed that any person skilled in the art who is using the preceding description can utilize the present invention to its fullest extent. The following examples are therefore to be interpreted as merely illustrative and not limiting of the disclosure in any way whatever.

PREPARATION EXAMPLES

Example-1: Synthesis of 2,3-Dichloropyridine

Step-1: Synthesis of 2-chlorobut-2-enenitrile from but-2-enenitrile

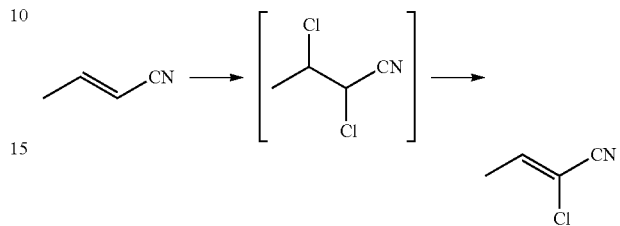

To a stirred solution of but-2-enenitrile (10 g, 149 mmol), pyridine (0.59 g, 7.45 mmol) and hydroquinone (0.41 g, 3.73 mmol) in dimethyl formamide (50 mL), chlorine gas was purged for 3-4 hours at 5-10° C. After completion of the reaction, nitrogen gas was purged into the reaction mixture until the pH reaches 5-7. Potassium carbonate (26.8 g, 194 mmol) was added portion wise into the reaction mixture over a period of 20 minutes at 0-5° C., and stirred further for 12 hours at 25-30° C. The reaction mass was quenched with water and extracted several times with dichloromethane (100 mL). The combined dichloromethane layers were dried over anhydrous sodium sulphate, filtered and concentrated under reduced pressure to obtain a crude product. The crude product was purified by vacuum distillation (30 mbar at 50° C.) to obtain 2-chlorobut-2-enenitrile (E/Z mixture).

GC-MS: MS: m/z=101.00

$^1$H-NMR: (400 MHz, CDCl$_3$-d$_6$) δ 6.71 (q, J=7.2 Hz, 1H), 1.92 (d, J=7.2 Hz, 3H) (major isomer). δ 6.21 (q, J=7.6 Hz, 1H), 2.01 (d, J=7.6 Hz, 3H) (minor isomer).

$^{13}$C-NMR: (100 MHz, CDCl$_3$-d$_6$) δ 143.3, 115.1, 105.0, 19.0 (major isomer). δ 144.7, 113.3, 103.1, 20.9 (minor isomer).

Step-2: Synthesis of 2-chloro-5-(dimethylamino) penta-2,4-dienenitrile from 2-chlorobut-2-enenitrile

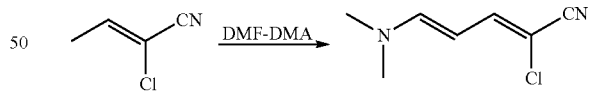

A mixture of 2-chlorobut-2-enenitrile (6.6 g, 65.0 mmol) and 1,1-dimethoxy-N,N-dimethylmethanamine (DMF-DMA) (28.9 g, 195.0 mmol) was stirred for 8-9 hours at 110° C. After completion of the reaction, excess of DMF-DMA was distilled off from the reaction mixture to obtain a crude product. The crude product was purified by crystallisation using methyl tert-butyl ether (MTBE) and n-hexane to obtain 2-chloro-5-(dimethylamino)penta-2,4-dienenitrile (E-Z mixture).

GC-MS: m/z 156.1 [M$^+$].

$^1$H-NMR: (400 MHz, CDCl$_3$) δ 6.83 (d, J=10.8 Hz, 1H), 6.72 (d, J=12.7 Hz, 1H), 5.08 (dd, J=12.7, 11.2 Hz 1H), 2.92 (s, 6H) (major isomer). δ 6.79-6.76 (m, 1H), 6.62 (d, J=12.8 Hz, 1H), 5.14-5.04 (m, 1H) (minor isomer).

Step-3: Synthesis of 2,3-dichloropyridine from 2-chloro-5-(dimethylamino)penta-2,4-dienenitrile

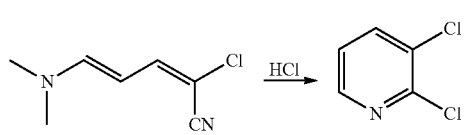

To a solution of 2-chloro-5-(dimethylamino)penta-2,4-dienenitrile (0.4 g, 2.55 mmol) in acetic acid (3.8 mL), dry hydrochloric acid gas was purged for 5 minutes at 15-20° C. The reaction mixture was further stirred further for 2-3 hours at 60° C. After the completion of reaction, saturated aqueous solution of potassium carbonate ($K_2CO_3$) was added dropwise at 0-5° C. The reaction mixture was extracted with dichloromethane (20 mL), the dichloromethane layer was dried over anhydrous sodium sulphate, filtered and concentrated under reduced pressure to obtain 2,3-dichloropyridine.

GC-MS: m/z 146.9 [M$^+$].

$^1$H-NMR: (400 MHz, DMSO-$d_6$) δ 8.41 (dd, J=1.6, 4.4 Hz, 1H), 8.14 (dd, J=1.6, 8.4 Hz, 1H), 7.48-7.45 (t, J=4.4, 8.4 Hz, 1H).

$^{13}$C-NMR: (100 MHz, DMSO-$d_6$) δ148.1, 147.5, 139.7, 129.3, 124.6.

Example-2: Synthesis of 2-bromo-3-chloropyridine

Synthesis of 2-bromo-3-chloropyridine from 2-chloro-5-(dimethylamino)penta-2,4-dienenitrile

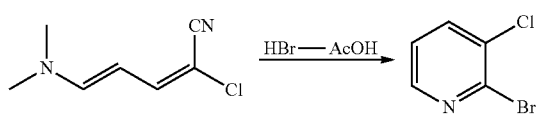

2-Chloro-5-(dimethylamino)penta-2,4-dienenitrile (0.5 g, 3.19 mmol) was added to a solution of hydrogen bromide (0.775 g, 9.58 mmol) in acetic acid (3 mL) at 25° C. The reaction mixture was stirred at 60° C. for 2-3 hours. After completion of the reaction, saturated aqueous solution of sodium bicarbonate (NaHCO$_3$) was added drop wise at 0-5° C. The reaction mixture was extracted with dichloromethane (20 mL), the dichloromethane layer was dried over sodium sulphate, filtered and concentrated under reduced pressure. The crude product was purified by silica-gel column chromatography to obtain 2-bromo-3-chloropyridine as a white solid.

GC-MS: m/z 192.8 [M$^+$]

$^1$H-NMR: (400 MHz, CDCl$_3$) δ 8.27 (dd, J=4.6, 1.5 Hz, 1H), 7.73 (dd, J=7.9, 1.5 Hz, 1H), 7.20-7.25 (m, 1H).

$^{13}$C-NMR: (100 MHz, CDCl$_3$) δ 147.6, 141.8, 138.3, 133.6, 123.5

Example-3: Synthesis of 2-butoxy-3-chloropyridine

Synthesis of 2-butoxy-3-chloropyridine from 2-chloro-5-(dimethylamino)penta-2,4-dienenitrile

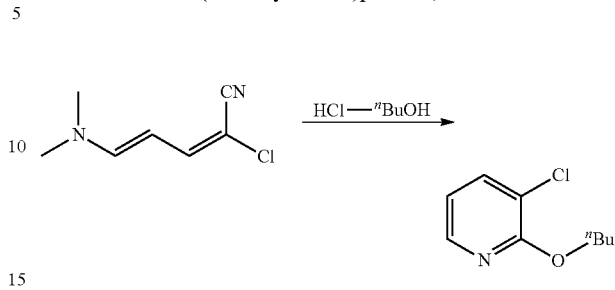

2-Chloro-5-(dimethylamino)penta-2,4-dienenitrile (0.5 g, 3.19 mmol) was added to a solution of hydrogen chloride (0.349 g, 9.58 mmol) in butanol (5 ml) at 25° C. The reaction mixture was stirred at 60° C. for 2-3 hours. After completion of the reaction, saturated aqueous solution of sodium bicarbonate (NaHCO$_3$) was added dropwise at 0-5° C. The reaction mixture was extracted with dichloromethane (20 mL), the dichloromethane layer was dried over anhydrous sodium sulphate, filtered and concentrated under reduced pressure. The crude product was purified by silica-gel column chromatography to obtain 2-butoxy-3-chloropyridine as a thick liquid.

GC-MS: m/z 184.9 [M$^+$].

$^1$H-NMR: (400 MHz, CDCl$_3$): δ 8.05 (dd, J=4.9, 1.7 Hz, 1H), 7.64 (dd, J=7.6, 1.7 Hz, 1H), 6.83 (dd, J=7.7, 5.0 Hz, 1H), 4.39 (t, 2H), 1.79-1.87 (m, 2H), 1.48-1.58 (m, 2H), 1.01 (t, 3H).

Example-4: Synthesis of 5,6-dichloronicotinaldehyde

Synthesis of 5,6-dichloronicotinaldehyde from 2-chlorobut-2-enenitrile

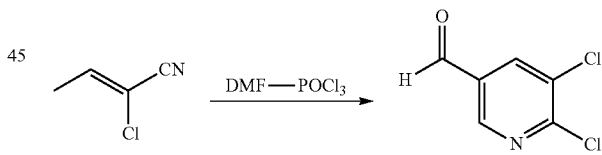

A mixture of phosphoryl chloride (0.688 ml, 7.39 mmol) and N,N-dimethylformamide (0.381 ml, 4.92 mmol) was stirred at 25° C. for 2 hours. 2-Chlorobut-2-enenitrile (0.5 g, 4.92 mmol) was added dropwise over a period of 30 minutes, and the resulting mixture was stirred at 80° C. for 2-3 hours. After completion of the reaction, the reaction mixture was poured into ice cold water and neutralized to pH 8 by adding aqueous sodium bicarbonate solution. The reaction mixture was extracted with dichloromethane (25 mL), the dichloromethane layer was dried over anhydrous sodium sulphate, filtered and concentrated under reduced pressure to obtain 5,6-dichloronicotinaldehyde.

GC-MS: m/z 175 [M$^+$].

$^1$HNMR: (400 MHz, CDCl$_3$): δ 10.07 (s, 1H), 8.75 (d, J=2 Hz, 1H), 8.22 (d, J=2 Hz, 1H).

$^{13}$CNMR: (100 MHz, CDCl$_3$): δ 188.1, 163.1, 148.9, 137.5, 131.9, 131.2.

Continuous Flow Process

Example-5: Synthesis of 2,3-dichloropyridine (2,3-DCP)

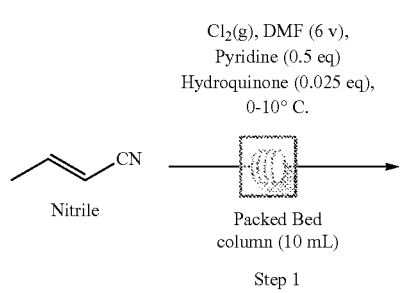

Step 1 (chlorination): 2,3-dichlorobutanenitrile (Di-Cl Int.)/2-chlorobut-2-enenitrile (C-Nitrile)

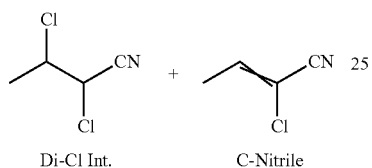

A stock solution of crotononitrile (2.1 M, 1.0 eq.) in N,N-dimethylformamide, pyridine (0.5 eq.) and hydroquinone (0.025 eq.) was prepared for pump A, which was connected to the reactor (MOC: SS, 10 mL) filled with glass beads via drop tubing. A separate tube (SS) from Cl$_2$-cylinder fitted with mass flow controller (MFC) was connected to the reactor. The temperature of the reactor was maintained between 0-10° C. with an ice/water jacket. Additional tubing was connected to the reactor to collect the crude reaction mixture. The residence time inside the reactor was set to 2 min with flow rates for pump A set to 5 mL/min and Cl$_2$-gas was purged at a rate of 2.96 g/min (2.0 eq.), which was controlled through MFC. Upon collection of a 1.0 mL sample of the crude product mixture, a sample was submitted for GC analysis, which showed conversion of the starting material into desired product C-Nitrile is 8.7% along with conversion into 2,3-dichlorobutanenitrile (di-Cl int) is 53.6%. Increasing the residence time up to 4 min with increased Cl$_2$ purging rate at 4.0 g/min (2.7 eq.) enhanced the conversion into C-Nitrile up to 13.5% was determined by GC analysis while conversion into di-Cl int is 50.2%.

Step 1a (Elimination): Synthesis of 2-chlorobut-2-enenitrile (C-Nitrile)

A stock solution containing a mixture of 2,3-dichlorobutanenitrile (71.92% Di-Cl Int.)/2-chlorobut-2-enenitrile (19.87% C-Nitrile) (1.03 M, 1.0 eq.) in N,N-dimethylformamide was prepared for pump A. This was connected to a glasss colum containing 1.0 g of K$_2$CO$_3$ cartridge (10 mL). The temperature of the reactor was maintained between 30-50° C. Additional tubing was connected to the other end of the cartridge of the reactor to collect the crude reaction mixture. Initially the residence time inside the reactor was set to 5 min with flow rates for pump A set to 2 mL/min at 30° C. Upon collection of approximately 10 mL sample of the crude product mixture, a sample was submitted for GC analysis, which exhibited conversion of the starting material into desired product C-Nitrile was 42.58% along with unreacted 2,3-dichlorobutanenitrile (Di-Cl int) was 37.53%. Further optimisation, by decreasing the residence time up to 1 min at elevated temperature of 50° C. enhanced C-Nitrile conversion 25.52%, but Di-Cl int. was degraded substantially to 14.70% which led to formation of several impurities determined by GC.

Step 2: Synthesis of 2-chloro-5-(dimethylamino)penta-2,4-dienenitrile (Enamine)

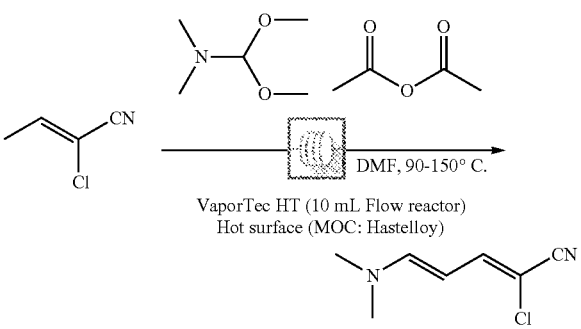

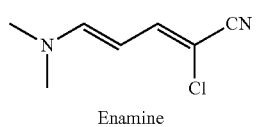

A stock solution of reactant C-nitrile, I (0.2 M in DMF, 1.0 eq., AI 30%) was prepared for pump A, DMF-DMA II (0.48 M in DMF) was prepared for pump B and catalyst Ac$_2$O III (0.08 M) was prepared for pump C. All three reactants were mixed with a T-mixer and heated with VaporTec Hot surface HT (10 mL Hastelloy) reactor for fixed residence time of 5 min. The reactor temperarture was kept at 150° C. and the residence time of 5 min. 3 molar equivalents of reactant II were mixed with reactant I. Under the above conditions, at-least 63% product conversion was observed.

Having described the invention with reference to certain preferred embodiments, other embodiments will become apparent to one skilled in the art from consideration of the specification. It will be apparent to those skilled in the art that many modifications, both to materials and methods, may be practiced without departing from the scope of the invention.

The invention claimed is:

1. A process for the preparation of a substituted pyridine of formula (I) or a salt thereof,

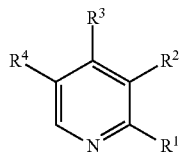

(I)

wherein,
$R^1$ is selected from the group consisting of halogens and $C_1$-$C_4$ alkoxy;
$R^2$ is selected from the group consisting of hydrogen, halogen, $C_1$-$C_4$ alkyl, $C_3$-$C_7$ cycloalkyl, $C_1$-$C_3$ haloalkyl, heterocyclyl, O—R', haloalkyl and O—C(O)R';
$R^3$ is selected from the group consisting of hydrogen, halogen $C_1$-$C_4$ alkyl, $C_3$-$C_7$ cycloalkyl, $C_1$-$C_3$ haloalkyl and $C_{1-3}$ alkoxy;
$R^4$ is selected from the group consisting of hydrogen, halogen, $C_1$-$C_4$ alkyl, $C_3$-$C_7$ cycloalkyl, $C_1$-$C_3$ haloalkyl, heterocyclyl, O—R', haloalkyl, O—C(O)R' and CHO;
R' is selected from the group consisting of $C_1$-$C_6$-alkyl and $C_1$-$C_3$ haloalkyl;
or
$R^2$ and $R^3$ or $R^3$ and $R^4$ can form a 5-6 membered carbocyclic or heterocyclic ring system, which is optionally substituted by halogen, $C_1$-$C_6$-alkyl, $C_1$-$C_6$-haloalkyl, $C_1$-$C_6$-alkoxy;
$R^2$, $R^3$ and $R^4$ groups are optionally substituted with halogen, CN, $C_1$-$C_6$-alkyl, $C_1$-$C_6$-haloalkyl, $C_1$-$C_6$-alkoxy;
comprising the steps of:
a) cyclizing a vinylogous nitrile of formula (II) or a salt thereof, by reacting with an acid (reagent-1) and optionally in the presence of a solvent; according to the reaction scheme-1 as depicted below:

Scheme-1

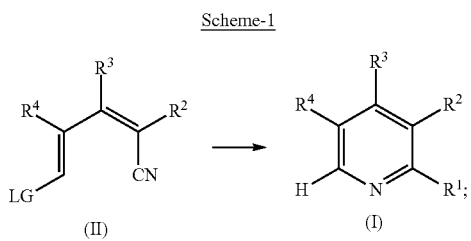

wherein LG represents OR' or $N(R')_2$; R', $R^1$, $R^2$, $R^3$ and $R^4$ are as defined above;
b) the vinylogous nitrile of formula (II) or a salt thereof, is obtained by reacting an α,β-unsaturated nitrile of formula (III) or a salt thereof, with reagent-2, and optionally in the presence of a catalyst and a solvent, according to the reaction scheme-2 as depicted below:

Scheme-2

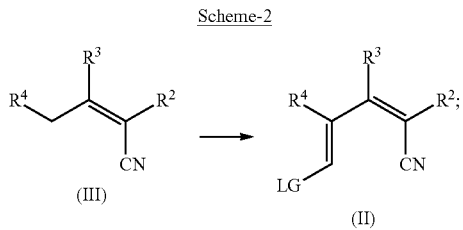

wherein $R^2$, $R^3$ and $R^4$ are as defined above.

2. The process according to claim 1, wherein the reagent-1 is an inorganic acid selected from hydrogen fluoride, hydrogen chloride or hydrogen bromide; a Lewis acid selected from titanium tetrachloride, boron trifluoride etherate, copper chloride, aluminium trichloride and zinc chloride.

3. The process according to claim 1, wherein reagent-2 is selected from:
  i. a compound of formula $(R^5)_2NCH(OR^5)_2$ or a salt thereof,
  ii. a compound of formula $(R^5)_2NCHO$ or a salt thereof and co-reagent (C-1),
  iii. an amine of formula $NH(R^5)_2$ or a salt thereof, a suitable ortho ester of formula $CR^7(OR^5)_3$ or a salt thereof and a co-reagent (C-2),
  iv. an ortho ester of formula $CR^7(R^6)_3$ or a salt thereof and a co-reagent (C-3),
  v. a formic acid/ester of formula $HCOOR^7$ or a salt thereof and a co-reagent (C-4),
  vi. an amine of formula $N(R^5)_3$ or a salt thereof and a co-reagent (C-5),
  vii. carbon monoxide and a co-reagent (C-4).

4. The process according to claim 1, wherein reagent-2 is selected from a compound of formula $(R^5)_2NCH(OR^5)_2$ or compound of formula $(R^5)_2NCHO$ or a salt thereof and co-reagent (C-1), or a salt thereof.

5. The process according to claim 1, wherein the solvent is selected from aliphatic, alicyclic or aromatic halogenated hydrocarbons, chlorobenzene, dichlorobenzene, dichloromethane, chloroform, tetrachloromethane, dichloroethane or trichloroethane; ethers, diethylether, diisopropyl ether, methyl tert-butyl ether, methyl tert-amyl ether, dioxane, tetrahydrofuran, 1,2-dimethoxy ethane, 1,2-diethoxyethane or anisole; nitriles, acetonitrile, propionitrile, n- or iso-butyronitrile or benzonitrile; amides, N,N-dimethylformamide, N,N-dimethylacetamide, N-methyl formanilide, N-methylpyrrolidone or hexamethylphosphoric triamide; sulfoxides, dimethyl sulfoxide or sulfones, sulfolane; alcohols, methanol, ethanol, isopropanol, polyethylene glycols; water or mixtures thereof.

6. The process according to claim 1, wherein the co-reagents are selected from:
  (C-1) represents phosphorous oxyhalides $(PO(X^1)_3)$; wherein $X^1$ represents halogen
  (C-2) and (C-3) represents one or more of p-toluenesulfonic acid, Lewis acids, $(Ac)_2O$, boron trifluoride $(BF_3)$, tetrafluoroboric acid $(HBF_4)$, zinc chloride $(ZnCl_2)$, aluminium chloride $(AlCl_3)$;

(C-4) represents one or more of sodium hydride (NaH), metal alkoxides, piperidine, pyridine, triethyl amine, N,N-diisopropylethylamine; and (C-5) represents N,N-dimethylformamide dimethyl sulfate adduct (DMF-DMS).

7. The process according to claim 1, wherein $R^1$ and $R^2$ represent halogen.

8. The process according to claim 1, wherein the α,β-unsaturated nitrile of formula (III) or a salt thereof,

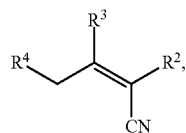
(III)

wherein $R^2$ represents halogen; $R^3$ and $R^4$ are as defined above, is prepared by, halogenating a substituted acrylonitrile of formula (III) or a salt thereof,

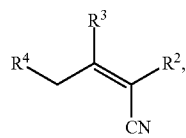
(III)

wherein $R^2$ represents hydrogen; $R^3$ and $R^4$ are as defined above;

in the presence of a halogenating reagent and optionally in the presence of a reagent-3 and a solvent.

9. The process according to claim 8, wherein the halogenating agent is selected from chlorine gas or hydrogen halogenides selected from hydrogen fluoride, hydrogen chloride or hydrogen bromide.

10. The process according to claim 8, wherein the halogention is performed in the presence of an oxidizing reagents selected from hydrogen peroxide.

11. The process according to claim 8, wherein the reagent-3 used for halogenation reaction is selected from pyridine, hydroquinone, piperidine, and triethyl amine.

12. The process according to claim 1, wherein, said process comprises the preparation of a substituted pyridine of formula (I-b) or a salt thereof,

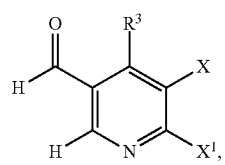
(I-b)

wherein X and $X^1$ represent halogen and $R^4$ is H or CHO; $R^3$ is as defined above;

comprising the step of:
reacting the compound of formula (III-c) or a salt thereof,

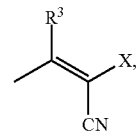
(III-c)

wherein X and $R^3$ are as defined above;
with a mixture of N,N-dimethylformamide and phosphorous oxyhalide (DMF-PO($X^1$)$_3$), to obtain a compound of formula (I-b) or a salt thereof.

13. The process according to claim 1, wherein the said process further comprises the preparation of a substituted 2-hydrazineyl pyridine of formula (IV) or a salt thereof,

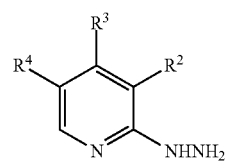
(VI)

wherein,
$R^2$ is selected from the group consisting of hydrogen, halogen, $C_1$-$C_4$ alkyl, $C_3$-$C_7$ cycloalkyl, $C_1$-$C_3$ haloalkyl, heterocyclyl, O—R', haloalkyl and O—C(O)R';
$R^3$ is selected from the group consisting of hydrogen, halogen $C_1$-$C_4$ alkyl, $C_3$-$C_7$ cycloalkyl, $C_1$-$C_3$ haloalkyl and $C_1$-3 alkoxy;
$R^4$ is selected from the group consisting of hydrogen, halogen, $C_1$-$C_4$ alkyl, $C_3$-$C_7$ cycloalkyl, $C_1$-$C_3$ haloalkyl, heterocyclyl, O—R', haloalkyl, O—C(O)R' and CHO;
R' is selected from the group consisting of $C_1$-$C_6$-alkyl and $C_1$-$C_3$ haloalkyl;
wherein $R^2$ and $R^3$ or $R^3$ and $R^4$ can form a 5-6 membered carbocyclic or heterocyclic ring system, which is optionally substituted by halogen, $C_1$-$C_6$-alkyl, $C_1$-$C_6$-haloalkyl, $C_1$-$C_6$-alkoxy;
$R^2$, $R^3$ and $R^4$ groups are optionally substituted with halogen, CN, $C_1$-$C_6$-alkyl, $C_1$-$C_6$-haloalkyl, $C_1$-$C_6$-alkoxy;
wherein, the said process comprises reacting a substituted pyridine compound of formula (I) as prepared according to the process according to claim 1, with a hydrazine source and optionally in presence of a base and a solvent, as depicted in scheme below:

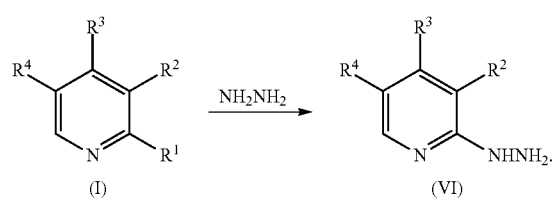

wherein $R^1$ is halogen

14. The process according to claim 1, wherein the said process comprises the preparation of the vinylogous nitrile of formula (II) or a salt thereof, wherein $R^2$ represent halogen,
comprising the steps of:
b) the vinylogous nitrile of formula (II) or a salt thereof, is obtained by reacting an α,β-unsaturated nitrile of formula (III) or a salt thereof, with reagent-2, and optionally in the presence of a catalyst and a solvent, according to the reaction scheme-2 as depicted below:

Scheme-2 c) the α,β-unsaturated nitrile of formula (III) or a salt thereof, is obtained by, halogenating a substituted acrylonitrile of formula (III) or a salt thereof, wherein $R^2$ represents hydrogen; $R^3$ and $R^4$ are as defined above; in the presence of a halogenating reagent and optionally in the presence of a reagent-3 and a solvent.

Scheme-2

15. The process according to claim 1, wherein LG present in the vinylogous nitrile of formula (II) or a salt thereof, is represented by —N(R$^5$)$_2$ wherein $R^5$ is selected from groups consisting of hydrogen, halogen, $C_1$-$C_4$ alkyl, $C_3$-$C_7$ cycloalkyl, $C_1$-$C_3$ haloalkyl, heterocyclyl, O—R', haloalkyl and O—C(O)R'.

16. The process according to claim 1, wherein the LG present in the vinylogous nitrile of formula (II) or a salt thereof, is represented by —OR$^5$ wherein $R^5$ is $C_1$-$C_6$ alkyl.

17. A continuous or semicontinuous flow process for the preparation of a compound of formula (I) or a salt thereof, (I)

wherein,
$R^1$ is selected from the group of halogens and $C_1$-$C_4$ alkoxy;
$R^2$ is selected from the group consisting of hydrogen, halogen, $C_1$-$C_4$ alkyl, $C_3$-$C_7$ cycloalkyl, $C_1$-$C_3$ haloalkyl, heterocyclyl, O—R', haloalkyl and O—C(O)R';

$R^3$ is selected from the group consisting of hydrogen, halogen $C_1$-$C_4$ alkyl, $C_3$-$C_7$ cycloalkyl, $C_1$-$C_3$ haloalkyl and $C_1$-$C_4$ alkoxy;
$R^4$ is selected from the group consisting of hydrogen, halogen, $C_1$-$C_4$ alkyl, $C_3$-$C_7$ cycloalkyl, $C_1$-$C_3$ haloalkyl, heterocyclyl, O—R', haloalkyl, O—C(O)R' and CHO;
R' is selected from the group consisting of $C_1$-$C_6$-alkyl and $C_1$-$C_3$ haloalkyl;
wherein $R^3$ and $R^4$ can form a 5-6 membered ring system, which is optionally substituted by halogen, $C_1$-$C_6$-alkyl, $C_1$-$C_6$-haloalkyl, $C_1$-$C_6$-alkoxy;
$R^3$ and $R^4$ groups are optionally substituted with halogen, CN, $C_1$-$C_6$-alkyl, $C_1$-$C_6$-haloalkyl, $C_1$-$C_6$-alkoxy;
comprising the steps of:
A. cyclizing a vinylogous nitrile of formula (II) or a salt thereof,
by reacting with a suitable acid (reagent-1) and optionally in the presence of a solvent; according to the reaction scheme-1 as depicted below:

Scheme-1 wherein LG represents OR' or N(R')$_2$; R', $R^1$, $R^2$, $R^3$ and $R^4$ are as defined above;
B. by reacting an α,β-unsaturated nitrile of formula (III) or a salt thereof, with reagent-2 selected from:
i. with a compound of formula (R$^5$)$_2$NCHO or a salt thereof and co-reagent (C-1)
or
ii. with a suitable amine compound of formula NH(R$^5$)$_2$ or a salt thereof, suitable ortho esters compound of formula CR$^7$(OR$^5$)$_3$ or a salt thereof and co-reagent (C-2),
and optionally in the presence of a suitable solvent, according to the reaction scheme-2 as depicted below:

Scheme-2 wherein, LG, co-reagents, $R^1$, $R^2$, $R^3$, $R^4$, $R^5$, $R^6$ and $R^7$ are as defined above.

18. A continuous or semicontinuous flow process for the preparation of a compound of formula (I) or salt thereof,

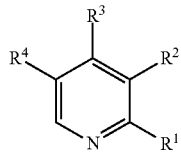

wherein,
$R^1$ and $R^2$ represents halogen;
$R^3$ is selected from the group consisting of hydrogen, halogen $C_1$-$C_4$ alkyl, $C_3$-$C_7$ cycloalkyl, $C_1$-$C_3$ haloalkyl and $C_1$-$C_4$ alkoxy;
$R^4$ is selected from the group consisting of hydrogen, halogen, $C_1$-$C_4$ alkyl, $C_3$-$C_7$ cycloalkyl, $C_1$-$C_3$ haloalkyl, heterocyclyl, O—R', haloalkyl, O—C(O)R' and CHO;
R' is selected from the group consisting of $C_1$-$C_6$-alkyl and $C_1$-$C_3$ haloalkyl;
wherein $R^3$ and $R^4$ can form a 5-6 membered ring system, which is optionally substituted by halogen, $C_1$-$C_6$-alkyl, $C_1$-$C_6$-haloalkyl, $C_1$-$C_6$-alkoxy;
$R^3$ and $R^4$ groups are optionally substituted with halogen, CN, $C_1$-$C_6$-alkyl, $C_1$-$C_6$-haloalkyl, $C_1$-$C_6$-alkoxy:
comprising the steps of:
A. cyclizing a vinylogous nitrile of formula (II) or a salt thereof, by reacting with a suitable acid (reagent-1) and optionally in the presence of a solvent, according to the reaction scheme-1 as depicted below:

Scheme-1

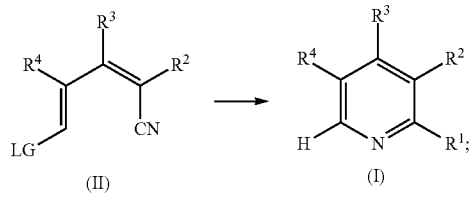

wherein LG represents OR' or N(R')$_2$; R' represents $C_1$-$C_6$-alkyl; $R^1$, $R^2$, $R^3$ and $R^4$ are as defined above;
B. by reacting an α,β-unsaturated nitrile of formula (III) or a salt thereof,
i. with a compound of formula (R$^5$)$_2$NCHO or a salt thereof and co-reagent (C-1)

or
ii. with a suitable amine compound of formula NH(R$^5$)$_2$ or a salt thereof, suitable ortho esters compound of formula CR$^7$(OR$^5$)$_3$ or a salt thereof and co-reagent (C-2),
and optionally in the presence of a suitable solvent, according to the reaction scheme-2 as depicted below:

Scheme-2

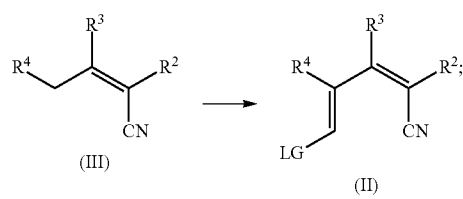

wherein, LG, co-reagents, $R^1$, $R^2$, $R^3$, $R^4$, $R^5$, $R^6$ and $R^7$ are as defined above;
C. obtaining the α,β-unsaturated nitrile of formula (III) or a salt thereof,
from a substituted acrylonitrile compounds of formula (III-b) or a salt thereof,
by halogenation, in the presence of a halogenating reagent and optionally in the presence of a reagent-3 and a suitable solvent, according to the reaction scheme-3a as depicted below:

Scheme-3a

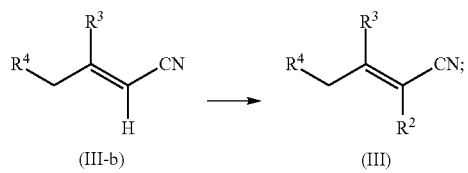

wherein $R^2$ is halogen; $R^3$ and $R^4$ are as defined above.
19. The process according to claim 14, wherein LG present in the vinylogous nitrile of formula (II) or a salt thereof, is represented by —N(R$^5$)$_2$ wherein $R^5$ is selected from groups consisting of hydrogen, halogen, $C_1$-$C_4$ alkyl, $C_3$-$C_7$ cycloalkyl, $C_1$-$C_3$ haloalkyl, heterocyclyl, O—R', haloalkyl and O—C(O)R'.
20. The process according to claim 14, wherein the LG present in the vinylogous nitrile of formula (II) or a salt thereof, is represented by —OR$^5$ wherein $R^5$ is $C_1$-$C_6$ alkyl.

* * * * *